United States Patent [19]

Terauchi et al.

[11] Patent Number: 4,460,705
[45] Date of Patent: Jul. 17, 1984

[54] CATALYST FOR OXIDATIVE DIMERIZATION

[75] Inventors: Takashi Terauchi, Iwaki; Koji Sato, Kita-Ibaraki; Shoichi Hoshi, Iwaki, all of Japan

[73] Assignee: Kureha Kagaku Kogyo Kabushiki Kaisha, Tokyo, Japan

[21] Appl. No.: 450,649

[22] Filed: Dec. 17, 1982

[30] Foreign Application Priority Data

Dec. 29, 1981 [JP]  Japan ................. 56-214257

[51] Int. Cl.$^3$ ............... B01J 23/02; B01J 23/04; B01J 23/08; B01J 23/10
[52] U.S. Cl. ................. 502/303; 502/302; 502/304; 502/328; 502/329; 502/330; 585/428
[58] Field of Search ............ 252/462, 463; 502/302, 502/303, 304, 328, 329, 330; 585/428

[56] References Cited

U.S. PATENT DOCUMENTS

| | | | |
|---|---|---|---|
| 3,476,747 | 11/1969 | Hargis et al. | 548/219 |
| 3,557,235 | 1/1971 | Henry et al. | 585/319 |
| 3,646,018 | 2/1972 | Duke et al. | 546/255 |
| 3,963,793 | 6/1976 | Weterings | 252/462 X |
| 4,247,727 | 1/1981 | Tremont | 585/428 |
| 4,268,704 | 5/1981 | Tremont et al. | 252/463 X |

FOREIGN PATENT DOCUMENTS

| | | |
|---|---|---|
| 0031654 | 7/1981 | European Pat. Off. |
| 48-34738 | 5/1973 | Japan |
| 2097278 | 11/1982 | United Kingdom |

*Primary Examiner*—W. J. Shine
*Attorney, Agent, or Firm*—Wegner & Bretschneider

[57] ABSTRACT

Disclosed is a catalyst for the oxidative dimerization of toluene, comprising a composition represented by the general formula:

$$Tl_1M_aM'_bO_c$$

wherein
M represents at least one element selected from the group consisting of beryllium, magnesium, calcium, strontium and barium; M' represents at least one element selected from the group consisting of lithium, sodium, potassium, rubidium, cesium, scandium, yttrium, lanthanum, cerium, praseodymium, neodymium, samarium, europium, gadolinium, terbium, dysprosium, holmium, erbium, thulium, ytterbium, lutetium, titanium, zirconium, hafnium, niobium, tantalum, zinc, aluminum, gallium, indium and antimony;

a is 0.05 to 15;
b is 0.05 to 15;
c is a number determined by the valences of thallium, M and M';

with the proviso that the number of alkali metal atoms is at most 20% of the number of total atoms constituting the catalyst except for oxygen when alkali metal is included in M', and a process for producing 1,2-diphenylethane and 1,2-diphenylethylene by the oxidative dimerization of toluene in the presence of a catalyst comprising a composition represented by the above-mentioned general formula.

1 Claim, No Drawings

CATALYST FOR OXIDATIVE DIMERIZATION

The present invention relates to a catalyst used in the production of dimers by the oxidative dimerization of toluene, and a process for the oxidative dimerization of toluene in the presence of the catalyst.

1,2-Diphenylethane or 1,2-diphenylethylene obtained by the oxidative dimerization of toluene are highly useful substances as the starting material for production of synthetic resins and paints, and the intermediate in various organic syntheses.

A number of processes for the oxidative dimerization of toluene to produce 1,2-diphenylethane or 1,2-diphenylethylene have been hitherto known. For instance, there are processes wherein each of halogens, sulfur or carbon disulfide is used as a hydrogen acceptor in the dehydrogenation (refer to Japanese Patent Laying Open No. 6312/74). In these processes, there are many demerits of forming corrosive substance(s), contaminating the object product with halides or sulfides and the high price of the hydrogen acceptor used in these conventional processes.

As another process, processes of using oxygen as the hydrogen acceptor have been known. And a number of processes of utilizing a metal oxide as the source of oxygen, the hydrogen acceptor, and as a catalyst of the reaction have recently been proposed. For instance, in U.S. Pat. No. 3,476,747, it is disclosed that bismuth oxide, antimony oxide, arsenic oxide and manganese arsenate are respectively effective in forming 1,2-bis-arylethylene by the oxidative dimerization of arylmethane. In Japanese Patent Publication No. 8088/69, a process for the oxidative dimerization of propylene or toluene by using lead oxide, cadmium oxide or thallium oxide as an oxidant has been disclosed. In Japanese Patent Publication No. 20561/74, it has been disclosed to use bismuth oxide, lead oxide, tellurium oxide, barium oxide, thallium oxide, cadmium oxide or mixture thereof as the source of oxygen in the oxidative dimerization of toluene.

Further, in Japanese Patent Laying Open No. 105602/75, a process for the oxidative dimerization of propylene, toluene, acetic acid or other compounds by the reaction with bismuth oxide or thallium oxide has been disclosed, and it has proposed that the catalytic activity of bismuth oxide or thallium oxide is improved by being supported on a basic carrier material of the specific surface area of larger than 20 m²/g. In addition, in U.S. Pat. No. 4,243,825, a process for the oxidative dimerization of toluene has been disclosed, wherein the "inorganic metal/oxygen composition" containing thallium and at least one element selected from the group consisting of arsenic, antimony, thorium, uranium, lanthanide and elements of the groups of IIIb, IVb, Vb and VIIb of the periodic table is used in the reaction.

As described the above, as catalysts for the dimerization of toluene, various kinds of metal oxides have been disclosed, however, none of them has given a satisfied result in the yield of dimers and in the selectivity of dimers.

An object of the present invention is to provide a process for producing 1,2-diphenylethane and 1,2-diphenylethylene at high yield by the oxidative dimerization of toluene.

Another object of the present invention is to provide a catalyst for advantageously producing 1,2-diphenylethane and 1,2-diphenylethylene by the oxidative dimerization of toluene.

Another object of the present invention is to provide a catalyst for remarkably improving toluene conversion and dimers selectivity in the oxidative dimerization of toluene.

A catalyst for the oxidative dimerization of toluene according to the present invention (hereinafter referred to as the present catalyst) is a multicomponent metal oxide comprising thallium oxide which is activated by both at least one alkaline earth metal oxide selected from the group consisting of beryllium oxide, magnesium oxide, calcium oxide, strontium oxide and barium oxide and at least one metal oxide selected from the group consisting of lithium oxide, sodium oxide, potassium oxide, rubidium oxide, cesium oxide, scandium oxide, yttrium oxide, lanthanum oxide, cerium oxide, praseodymium oxide, neodymium oxide, samarium oxide, europium oxide, gadolinium oxide, terbium oxide, dysprosium oxide, holmium oxide, erbium oxide, thulium oxide, ytterbium oxide, lutetium oxide, titanium oxide, zirconium oxide, hafnium oxide, niobium oxide, tantalum oxide, zinc oxide, aluminum oxide, gallium oxide, indium oxide and antimony oxide. That is, the present catalyst comprises a composition represented by the general formula:

$$Tl_1 M_a M'_b O_c$$

wherein

M represents at least one element selected from the group consisting of beryllium, magnesium, calcium, strontium and barium;

M' represents at least one element selected from the group consisting of lithium, sodium, potassium, rubidium, cesium, scandium, yttrium, lanthanum, cerium, praseodymium, neodymium, samarium, europium, gadolinium, terbium, dysprosium, holmium, erbium, thulium, ytterbium, lutetium, titanium, zirconium, hafnium, niobium, tantalum, zinc, aluminum, gallium, indium and antimony;

a is 0.05 to 15;

b is 0.05 to 15;

c is a number determined by the valences of thallium, M and M'; with the proviso that the number of alkali metal atoms is at most 20 % of the number of total atoms constituting the catalyst except for oxygen when alkali metal is included in M'. And preferred composition are those represented by the above-mentioned general formula wherein a plus b is 0.5 to 19.

The present catalyst exhibits high conversion and high selectivity in the oxidative dimerization of toluene when three kinds of elements of thallium, M and M' coexist to activate thallium with M and M', and the catalyst which lacks at least one of thallium, M and M' cannot be effective as shown in the following Examples.

The present catalyst can be obtained by uniformly blending the weighted raw materials which correspond to the above-mentioned ratios, forming the mixture into a desirable shape if necessary, drying and calcining. The raw material is a compound containing the metal element which constitutes the present catalyst, i.e. thallium, M and M'. And the metal compounds such as oxides, hydroxides, nitrates, carbonates and acetates may be used.

Several non-limitative methods for preparing the present catalyst are shown as follows.

In one of the simplest methods for preparing the present catalyst, powdery metal oxides are respectively weighted to give the desired ratio, uniformly blended in a dried state in a morter, a ball mill, a mixer or the like, and then baked. As other methods, the following methods can be mentioned:

(a) Powdery oxides of metals are mixed well in a dried state, and after water is added to the mixture, the mixture is well mixed to be a paste-like material, and forming the paste-like material into a desirable shape, drying and calcining.

(b) Desired metal compounds such as oxides, hydroxides, nitrates, carbonates and acetates are mixed well in water or nitric acid, and then the solution is heated in the air to evaporate moisture and further calcined in the air to be converted into the desired metal oxide by pyrolysis.

(c) After mixing the desired metal compounds such as nitrates, carbonates, acetates, hydroxides and oxides sufficiently in water or nitric acid, a precipitant such as aqueous ammonia is added and after collecting the co-precipitate by filtering the resulting slurry, the co-precipitate is washed with water, formed, dried and calcined in the air. (d) After the co-precipitate is obtained in (c), water is added to the co-precipitate again. Then the resulting slurry is spray-dried to be shaped like free-flowing spherical particles and calcined.

The calcination step in the above-mentioned methods for preparing the present catalyst may be carried out at a temperature in the range of 500 to 1,000° c., preferably 600 to 900° C. The time period for calcining is 0.5 to 30 hours.

The oxidative dimerization of toluene to produce 1,2-diphenylethane and 1,2-diphenylethylene according to the present invention (hereinafter referred to as the present process) is carried out in a gas phase in the presence of the present catalyst at 400 to 650° C., preferably 450 to 630° C. while introducing a preheated gas containing toluene into the reactor. Toluene may be supplied singly or may be supplied after diluting with an inert gas such as nitrogen or helium.

In the present process, it is preferable to mix toluene vapour with steam since the coexistence of steam and toluene vapour shows the effect of suppressing the formation of carbon dioxide by the complete oxidation of toluene. The preferable molar ratio of water to toluene is in a range of 0.2 to 5. In addition, toluene may be supplied as a liquid into the reactor wherein the liquid is evaporated and brought into the reaction zone.

The contact time between toluene and the present catalyst in the present process is within 0.1 to 60 seconds, preferably 0.2 to 20 seconds.

Further, the reaction is usually carried out at the atmospheric pressure, and may be carried out at a pressure of 0.1 to 5 atm, if necessary.

In cases of carrying out the present process, the catalyst may be used in any mode of fixed bed-type, fluidized bed-type or moving bed-type. On using a catalyst as fixed bed in the present process, one or more reactor(s) may be employed. Oxygen which is necessary for the reaction is not free oxygen molecules but oxygen atoms which are present in the present catalyst as a component of metal oxides, and as a result, a partial reduction of the catalyst occurs when the present catalyst participates in the reaction. Consequently, it is necessary to oxidize the reduced catalyst to regenerate the catalytic activity by a method suitable for the progress of the reaction. Such a regeneration of the catalyst is easily carried out by heating the reduced catalyst at a temperature of 400 to 700° C. in the air or in the gas containing oxygen for 5 sec. to 30 min. In a case of using a catalyst as fixed bed the operation of the regeneration may be carried out without taking the spent catalyst out of the reactor, but the dimerization and the regeneration are alternately carried out in a reactor. On the other hand, in a case of using a catalyst as fluidized bed or moving bed, a part of the catalyst containing the spent catalyst may be continuously taken out of the reactor and regenerated in a separate place, and then the regenerated catalyst is returned to the reactor in circulation. In the latter case, it is not necessary to discontinuate the dimerization.

The dimers obtained in the present process are taken out of the reactor with by-products and unreacted toluene can be extracted from the mixture and purified. On the other hand, the unreacted toluene can be used again as the reactant.

The present invention will be explained more in detail; it will be apparent that the conversion of toluene and the yield of dimers are remarkably improved in the oxidative dimerization of toluene by the use of the present catalyst. While the present invention is described with respect to the examples as is mentioned hereinafter, it can be understood that the examples as is mentioned hereinafter is disclosed to explain the present invention and that the invention is not limited thereto.

EXAMPLE 1

Preparation of the present catalyst

1—1;

After 289.8 g of $Tl_2O_3$, 204.5 g of MgO and 5.7 g of $Li_2O_3$ were weighted respectively, they were blended; then 200 g of water was added to the mixture, the whole mixture was well blended again and heated to evaporate a part of the water. Consequently a paste-like mixture was obtained. After dividing the paste-like mixture into desired cakes followed by drying in the air at 150° C. for 10 hours, the dried cakes were calcined for 5 hours in the air at 700° C. After cooling the calcined cakes they were pulverized and sifted to the particles passing through Tylor #20 mesh sieve and stopping on Tylor #30 mesh sieve. The atomic ratio of the metal elements constituting the material was $Tl:Mg:Li=1:4.0.3$.

1-2:

In the same procedure as in Example 1—1, a calcined material was obtained from 273.0 g of $Tl_2O_3$, 144.6 g of MgO and 82.4 g of $Sc_2O_3$. The atomic ratio of the metal elements constituting the material was $Tl:Mg:Sc=1:3:1$.

1-3:

In the same procedure as in Example 1—1, a calcined material was obtained from 130.7 g of $Tl_2O_3$, 46.1 g of MgO and 323.1 g of $Y_2O_3$. The atomic ratio of the metal elements constituting the material was $Tl:Mg:Y=1:2:5$.

1-4:

In the same procedure as in Example 1—1, a calcined material was obtained from 210.4 g of $Tl_2O_3$, 185.6 g of MgO and 104.0 g of $Y_2O_3$. The atomic ratio of the metal elements constituting the material was $Tl:Mg:Y=1:5:1$.

1-5:

In the same procedure as in Example 1—1, a calcined material was obtained from 270.7 g of $Tl_2O_3$, 95.5 g of MgO and 133.8 g of $Y_2O_3$. The atomic ratio of the metal elements constituting the material was $Tl:Mg:Y=1:2:1$.

1-6:

In the same produre as in Example 1—1, a calcined material was obtained from 374.4 g of $Tl_2O_3$, 33.0 g of MgO and 92.6 g of $Y_2O_3$. The atomic ratio of the metal elements constituting the material was Tl:Mg:Y=1:0.5:0.5.

1-7:

In the same procure as in Example 1—1, a calcined material was obtained from 158.5 g of $Tl_2O_3$, 153.34 g of BaO and 235.1 g of $Y_2O_3$. The atomic ratio of the metal elements constituting the material was Tl:Ba:Y=1:1:3.

1-8:

After 265.1 g of $Tl_2O_3$, 140.3 g of MgO and 94.6 g of $La_2O_3$ were weighed respectively, they were blended, than 200 g of water was added to the mixture, the whole mixture was well blended again and heated to evaporate a part of the water consequently a past-like mixture was obtained. After dividing the paste-like mixture into desired cakes followed by drying in the air at 150° C. for 10 hours, the dried cakes were calcined at first at 400° C. for 2 hours in the air and then at 700° C. for 12 hours in the air. After cooling the calcined cakes, they wer pulverized and sifted to the particles passing through Tylor #20 mesh sieve and stopping on Tylor #30 mesh sieve. The atomic ratio of the metal elements constituting the material was Tl:Mg:La=1:3:0.5.

1-9:

In the same procedure as in Example 1—1, a calcined material was obtained from 275.0 g of $Tl_2O_3$, 121.4 g of MgO and 103.6 g of $CeO_2$. The atomic ratio of the metal elements constituting the material was Tl:Mg:Ce=1:2.5:0.5.

1-10:

In the same procedure as in Example 1—1, a calcined material was obtained from 229.6 g of $Tl_2O_3$, 101.3 g of MgO and 169.1 g of $Nd_2O_3$. The atomic ratio of the metal elements constituting the material was Tl:Mg:Nd=1:2.5:1.

1-11:

In the same procedure as in Example 1-8, a calcined material was obtained from 257.3 g of $Tl_2O_3$, 136.3 g of MgO and 106.4 g of $Ho_2O_3$. The atomic ratio of the metal elements constituting the material was Tl:Mg:Ho=1:3:0.5.

1-12:

In the same procedure as in Example 1—1, a calcined material was obtained from 255.0 g of $Tl_2O_3$, 135.0 g of MgO and 110.0 g of $Yb_2O_3$. The atomic ratio of the metal elements constituting the material was Tl:Mg:Yb=1:3:0.5.

1-13:

In the same procedure as in Example 1-8, a calcined material was obtained from 327.2 g of $Tl_2O_3$, 115.5 g of MgO and 57.2 g of $TiO_2$. The atomic ratio of the metal elements constituting the material was Tl:Mg:Ti=1:2:0.5.

1-14:

In the same procedure as in Example 1-8, a calcined material was obtained from 240.1 g of $Tl_2O_3$, 217.9 g of SrO and 42.0 g of $TiO_2$. The atomic ratio of the metal elements constituting the material was Tl:Sr:Ti=1:2:0.5.

1-15:

In the same procedure as in Example 1—1, a calcined material was obtained from 167.4 g of $Tl_2O_3$, 61.7 g of CaO and 271.0 g of $ZrO_2$. The atomic ratio of the metal elements constituting the material was Tl:Ca:Zr=1:1.5:3.

1-16:

In the same procedure as in Example 1—1, a calcined material was obtained from 133.3 g of $Tl_2O_3$, 121.0 g of SrO and 245.7 g of $HfO_2$. The atomic ratio of the metal elements constituting the material was Tl:Sr:Hf=1:2:2.

1-17:

In the same procedure as in Example 1—1, a calcined material was obtained from 218.5 g of $Tl_2O_3$, 154.3 g of MgO and 127.2 g of $Nb_2O_3$. The atomic ratio of the metal elements constituting the material was Tl:Mg:Nb—1:4:1.

1-18:

In the same procedure as in Example 1-8, a calcined material was obtained from 187.0 g of $Tl_2O_3$, 132.0 g of MgO and 180.9 g of $Ta_2O_5$. The atomic ratio of the metal elements constituting the material was Tl:Mg:Ta=1:4:1.

1-19:

In the same procedure as in Example 1—1, a calcined material was obtained from 265.1 g of $Tl_2O_3$, 140.4 g of MgO and 94.5 g of ZnO. The atomic ratio of the metal elements constituting the material was Tl:Mg:Zn=1:3:1.

1-20:

In the same procedure as in Example 1—1, a calcined material was obtained from 232.3 g of $Tl_2O_3$, 164.0 g of MgO and 103.7 g of $Al_2O_3$. The atomic ratio of the metal elements constituting the material was Tl:Mg:Al=1:4:2.

1-21:

In the same procedure as in Example 1—1, a calcined material was obtained from 239.5 g of $Tl_2O_3$, 211.4 g of MgO and 49.1 g of $Ga_2O_3$. The atomic ratio of the metal elements constituting the material was Tl:Mg:Ga=1:5:0.5.

1-22:

In the same procedure as in Example 1—1, a calcined material was obtained from 244.4 g of $Tl_2O_3$, 107.1 g of BeO and 148.6 g of $In_2O_3$. The atomic ratio of the metal elements constituting the material was Tl:Be:In=1:4:1.

1-23:

In the same procedure as in Example 1-8, a calcined material was obtained from 284.0 g of $Tl_2O_3$, 125.3 g of MgO and 90.6 g of $Sb_2O_3$. The atomic ratio of the metal elements constituting the material was Tl:Mg:Sb=1:2.5:0.5.

1-24:

In the same procedure as in Example 1—1, a calcined material was obtained from 230.8 g of $Tl_2O_3$, 81.5 g of MgO, 114.1 g of $Y_2O_3$ and 73.6 g of $Sb_2O_3$. The atomic ratio of the metal elements constituting the material was Tl:Mg:Y:Sb=1:2:1:0.5.

1-25:

In the same procedure as in Example 1—1, a calcined material was obtained from 226.1 g of $Tl_2O_3$, 79.8 g of MgO, 111.8 g of $Y_2O_3$, 72.2 g of $Sb_2O_3$ and 10.1 g of RbOH. The atomic ratio of the metal elements constituting the material was Tl:Mg:Y:Sb:Rb=1:2:1:0.5:0.1.

1-26:

In the same procedure as in Example 1—1, a calcined material was obtained from 127.8 g of $Tl_2O_3$, 58.0 g of SrO, 63.2 g of $Y_2O_3$ and 251.0 g of $Al_2O_3$. The atomic ratio of the metal elements constituting the material was Tl:Sr:Y:Al=1:1:1:8.8.

1-27:

In the same procedure as in Example 1—1, a calcined material was obtained from 170.2 g of $Tl_2O_3$, 30.0 g of MgO, 77.2 g of SrO, 168.3 g of $Y_2O_3$ and 54.3 g of $Sb_2O_3$. The atomic ratio of the metal elements constituting the material was Tl:Mg:Sr:Y:Sb=1:1:1:2:0.5.

1-28:

In the same procedure as in Example 1—1, a calcined material was obtained from 158.8 g of $Tl_2O_3$, 56.1 g of MgO, 72.0 g of SrO, 119.7 g of $CeO_2$, 85.7 g of $ZrO_2$ and 7.8 g of KOH. The atomic ratio of the metal elements constituting the material was Tl:Mg:Sr:Ce:Zr:K=1:2:1:1:1:0.2.

EXAMPLE 2

Oxidative dimerization of toluene

A stainless-steel pipe, 25 mm in internal diameter and 1,000 mm in length, was employed as a reactor. The reactor was charged with 150 ml of the present catalyst prepared in Example 1. The oxidative dimerization of toluene was carried out by heating the charged reactor to a predetermined temprature by a heater set around the outer wall of the pipe and by feeding toluene and water to the reactor. The rate of toluene was 120 ml/hr as liquid at 25° C. and that of water was 42 ml/hr as liquid 25° C. The reaction was carried out for 10 minutes. The reaction effluent was collected into a catcher at the outlet of the reactor, and then analyzed by gas-chromatography.

From the results of gas-chromatographic analysis, the conversion of toluene (amount of reacted toluene/amount of supplied toluene), the selectivity (amount of dimers, amount of benzene and amount of carbon dioxide, respectively to the amount of total products) and the yield (amount of toluene converted into dimers/amount of suppied toluene) were calculated and shown in Table 1 together with the reaction condition. In Table 1, the dimers mean the sum of 1,2-diphenylethane and 1,2-diphenylethylene.

COMPARATIVE EXAMPLE 1

The oxidative dimerization of toluene was carried out in the same apparatus and in the same procedures as in Example 2 except for charging the reactor with each of thallium oxide, magnesium oxide and yttrium oxide instead of the present catalyst in Example 1. The results are shown in Table 1.

As are seen in Table 1, the use of the present catalyst in the oxidative dimerization of toluene gave a remarkably improved conversion of toluene, and also a remarkably improved yield of the dimers as compared with the results when a single metal oxide was used as the catalyst.

COMPARATIVE EXAMPLE 2

The oxidative dimerization of toluene was carried out in the same apparatus and in the same procedures as in Example 2 except for charging the reactor with each of the binary metal oxides consisting of any two metal elements in Tl, M and M' which are the metal elements constituting the present catalyst. The results are shown in Table 1. The catalyst of Runs 1, 2, 3, 4, 8, 9 and 11 in Comparative Example 2 in Table 1 were prepared by the same procedure as in 1—1 of Example 1 from a total of 500 g metal oxides and the catalysts of Runs 5, 6, 7 and 10 were prepared by the same procedure as in 1-8 of Example 1 from a total of 500 g metal oxides. As are seen in Table 1, the use of any binary metal oxides, combining any two metals which are the elements constituting the present catalyst was not effective in the oxidative dimerization of toluene.

COMPARATIVE EXAMPLE 3

The oxidative dimerization of toluene was carried out in the same apparatus and in the same procedures as in Example 2 except for charging the reactor with a ternary metal oxides comprising thallium oxide, magnesium oxide and yttrium oxide which had the atomic ratio of Tl:Mg:Y outside that of the present catalyst. The catalyst was prepared by the same procedure as in 1—1 of Example 1 from a total of 500 g metal oxides. The results are shown in Table 1.

As are seen in Table 1, the use of the present catalyst in the oxidative dimerization of toluene has greatly improved the conversion of toluene and the selectivity of dimers.

It has verified by the result of Example and Comparative Examples that the present catalyst is a remarkably effective catalyst in the oxidative dimerization of toluene.

TABLE 1

| Classification | Run | Composition of catalyst (atomic ratio of metals) | | Reaction temperature (°C.) | Conversion of toluene (%) | Yield of dimers (%) | Selectivity of products (%) | | |
|---|---|---|---|---|---|---|---|---|---|
| | | | | | | | Dimers | Benzene | Carbon dioxide |
| Example 2 | (1) | Tl—Mg—Li; | 1-4-0.3 | 600 | 41.1 | 21.4 | 52.1 | 10.5 | 25.2 |
| | (2) | Tl—Mg—Sc; | 1-3-1 | 600 | 37.5 | 22.5 | 59.9 | 13.6 | 11.3 |
| | (3) | Tl—Mg—Y; | 1-2-5 | 550 | 37.0 | 30.1 | 81.4 | 5.3 | 2.9 |
| | | | | 600 | 48.5 | 37.2 | 76.7 | 5.6 | 3.7 |
| | (4) | Tl—Mg—Y; | 1-5-1 | 550 | 25.7 | 21.1 | 82.0 | 5.0 | 2.7 |
| | | | | 600 | 43.2 | 32.3 | 74.7 | 7.6 | 4.5 |
| | (5) | Tl—Mg—Y; | 1-2-1 | 550 | 43.0 | 28.0 | 65.0 | 13.8 | 6.7 |
| | | | | 600 | 58.0 | 31.1 | 53.6 | 22.2 | 9.3 |
| | (6) | Tl—Mg—Y; | 1-0.5-0.5 | 600 | 27.8 | 21.2 | 76.2 | 4.3 | 9.1 |
| | (7) | Tl—Ba—Y; | 1-1-3 | 600 | 29.6 | 22.3 | 75.3 | 4.9 | 8.4 |
| | (8) | Tl—Mg—La; | 1-3-0.5 | 600 | 51.5 | 31.0 | 60.1 | 17.2 | 7.7 |
| | (9) | Tl—Mg—Ce; | 1-2.5-0.5 | 600 | 34.1 | 26.2 | 76.7 | 5.4 | 6.5 |
| | (10) | Tl—Mg—Nd; | 1-2.5-1 | 600 | 43.9 | 27.4 | 62.5 | 12.2 | 10.2 |
| | (11) | Tl—Mg—Ho; | 1-3-0.5 | 600 | 34.3 | 24.9 | 72.5 | 6.0 | 9.4 |
| | (12) | Tl—Mg—Yb; | 1-3-0.5 | 600 | 36.1 | 25.3 | 70.2 | 5.7 | 10.8 |
| | (13) | Tl—Mg—Ti; | 1-2-0.5 | 600 | 31.0 | 24.6 | 79.2 | 2.6 | 6.9 |
| | (14) | Tl—Sr—Ti; | 1-2-0.5 | 500 | 27.5 | 21.9 | 79.8 | 1.4 | 6.2 |
| | | | | 600 | 36.4 | 23.7 | 65.1 | 12.7 | 8.3 |
| | (15) | Tl—Ca—Zr; | 1-1.5-3 | 600 | 32.7 | 22.6 | 69.1 | 9.2 | 6.6 |
| | (16) | Tl—Sr—Hf; | 1-2-2 | 600 | 35.5 | 25.7 | 72.3 | 8.1 | 7.5 |
| | (17) | Tl—Mg—Nb; | 1-4-1 | 600 | 37.2 | 25.7 | 69.0 | 8.8 | 8.9 |
| | (18) | Tl—Mg—Ta; | 1-4-1 | 600 | 28.6 | 23.7 | 82.7 | 5.3 | 1.4 |
| | (19) | Tl—Mg—Zn; | 1-3-1 | 600 | 36.7 | 24.8 | 67.7 | 10.1 | 4.6 |

TABLE 1-continued

| Classification | Run | Composition of catalyst (atomic ratio of metals) | | Reaction temperature (°C.) | Conversion of toluene (%) | Yield of dimers (%) | Selectivity of products (%) | | |
|---|---|---|---|---|---|---|---|---|---|
| | | | | | | | Dimers | Benzene | Carbon dioxide |
| | (20) | Tl—Mg—Al; | 1-4-2 | 600 | 32.5 | 25.5 | 78.4 | 5.2 | 1.5 |
| | (21) | Tl—Mg—Ga; | 1-5-0.5 | 600 | 34.9 | 26.7 | 76.6 | 5.1 | 4.8 |
| | (22) | Tl—Be—In; | 1-4-1 | 600 | 41.8 | 27.3 | 65.3 | 7.2 | 11.0 |
| | (23) | Tl—Mg—Sb; | 1-2.5-0.5 | 550 | 30.2 | 24.7 | 81.9 | 5.7 | 4.3 |
| | | | | 600 | 50.5 | 36.2 | 71.6 | 11.0 | 5.6 |
| | (24) | Tl—Mg—Y—Sb; | 1-2-1-0.5 | 550 | 33.7 | 26.2 | 77.7 | 9.8 | 6.2 |
| | | | | 600 | 45.4 | 32.1 | 70.7 | 13.0 | 7.3 |
| | (25) | Tl—Mg—Y—; Sb—Rb | 1-2-1-0.5-0.1 | 550 | 41.3 | 31.8 | 77.0 | 6.5 | 7.3 |
| | | | | 600 | 56.2 | 41.1 | 73.2 | 8.8 | 9.0 |
| | (26) | Tl—Sr—Y—Al; | 1-1-1-8.8 | 550 | 35.9 | 29.6 | 82.5 | 4.9 | 2.9 |
| | | | | 600 | 44.0 | 32.3 | 73.5 | 10.6 | 3.6 |
| | (27) | Tl—Mg—Sr—; Y—Sb | 1-1-1-2-0.5 | 600 | 43.4 | 29.8 | 68.7 | 9.3 | 7.1 |
| | (28) | Tl—Mg—Sr—; Ce—Zr—K | 1-2-1-1-1-0.2 | 600 | 36.6 | 26.0 | 71.1 | 8.9 | 7.7 |
| Comparative Example 1 | (1) | Tl$_2$O$_3$ | | 600 | 11.3 | 8.4 | 74.5 | 5.3 | 10.6 |
| | (2) | MgO | | 600 | 0.9 | 0.7 | 82.1 | 7.6 | 2.1 |
| | (3) | Y$_2$O$_3$ | | 600 | 5.1 | 4.1 | 80.3 | 7.7 | 4.1 |
| Comparative Example 2 | (1) | Tl—Mg; | 1-0.5 | 600 | 17.0 | 9.7 | 57.1 | 18.3 | 10.6 |
| | (2) | Tl—Mg; | 1-5 | 550 | 29.1 | 13.4 | 46.0 | 20.2 | 23.5 |
| | | | | 600 | 35.2 | 14.6 | 41.6 | 27.8 | 14.3 |
| Comparative Example 2 | (3) | Tl—Ba; | 1-1 | 600 | 18.4 | 12.8 | 69.5 | 13.7 | 8.5 |
| | | | | 550 | 15.9 | 9.3 | 58.3 | 11.5 | 20.0 |
| | (4) | Tl—Y; | 1-1 | 600 | 29.1 | 15.9 | 54.5 | 21.3 | 15.2 |
| | (5) | Tl—La; | 1-1 | 600 | 24.0 | 9.0 | 37.3 | 32.5 | 18.6 |
| | (6) | Tl—Ho; | 1-1 | 600 | 19.4 | 9.5 | 49.1 | 20.3 | 16.9 |
| | (7) | Tl—Ti; | 1-2 | 600 | 9.5 | 8.1 | 85.2 | 5.6 | 2.0 |
| | (8) | Tl—Zr; | 1-2 | 600 | 31.3 | 15.7 | 50.1 | 20.6 | 14.1 |
| | (9) | Tl—Zn; | 1-2 | 600 | 33.1 | 16.0 | 48.4 | 16.9 | 20.1 |
| | (10) | Tl—Sb; | 1-0.5 | 550 | 16.6 | 13.3 | 80.1 | 0.9 | 8.7 |
| | | | | 600 | 21.2 | 15.6 | 73.8 | 3.4 | 13.4 |
| | (11) | Mg—Y; | 1-1 | 600 | 5.8 | 4.8 | 82.1 | 6.1 | 2.3 |
| Comparative Example 3 | (1) | Tl—Mg—Y; | 1-0.01-0.01 | 600 | 13.8 | 10.5 | 76.0 | 7.1 | 7.5 |
| | (2) | Tl—Mg—Y; | 1-25-25 | 600 | 14.6 | 10.4 | 71.2 | 9.4 | 8.8 |

What is claimed is:

1. A catalyst for the oxidative dimerization of toluene, consisting essentially of a composition represented by the general formula:

$$Tl_1M_aM'_bO_c$$

wherein

M represents at least one element selected from the group consisting of beryllium, magnesium, calcium, strontium and barium; M' represents at least one element selected from the group consisting of lithium, sodium, potassium, rubidium, cesium, scandium, yttrium, lanthanum, cerium, praseodymium, neodymium, samarium, europium, gadolinium, terbium, dysprosium, holmium, erbium, thulium, ytterbium, lutetium, titanium, zirconium, hafnium, niobium, tantalum, zinc, aluminum, gallium, indium and antimony;

a is 0.05 to 15;

b is 0.05 to 15;

c is a number determined by the valences of thallium, M and M'; with the proviso that the number of alkali metal atoms is at most 20% of the number of total atoms constituting the catalyst except for oxygen when alkali metal is included in M'.

* * * * *